US008795270B2

(12) United States Patent
Drake (10) Patent No.: US 8,795,270 B2
(45) Date of Patent: Aug. 5, 2014

(54) SYSTEM AND METHOD FOR ABLATING TISSUE

(75) Inventor: Scott Drake, Niwot, CO (US)

(73) Assignee: Covidien AG (CH)

( * ) Notice: Subject to any disclaimer, the term of this patent is extended or adjusted under 35 U.S.C. 154(b) by 1860 days.

(21) Appl. No.: 11/409,832

(22) Filed: Apr. 24, 2006

(65) Prior Publication Data

US 2007/0250054 A1     Oct. 25, 2007

(51) Int. Cl.
*A61B 18/14*     (2006.01)
*A61B 18/00*     (2006.01)

(52) U.S. Cl.
CPC ..... *A61B 18/1487* (2013.01); *A61B 2018/0016* (2013.01); *A61B 2018/00577* (2013.01)
USPC .............................. 606/41; 606/45

(58) Field of Classification Search
CPC ............. A61B 18/1477; A61B 18/148; A61B 18/1487; A61B 2018/0016; A61B 2018/00577; A61B 2018/143
USPC ................................ 606/41, 45; 607/105, 113
See application file for complete search history.

(56) References Cited

U.S. PATENT DOCUMENTS

| | | | |
|---|---|---|---|
| 4,074,718 A | 2/1978 | Morrison, Jr. et al. | |
| 4,411,266 A | 10/1983 | Cosman | |
| 4,565,200 A | 1/1986 | Cosman | |
| 4,576,177 A | 3/1986 | Webster, Jr. | |
| 4,608,977 A | 9/1986 | Brown | |
| 4,662,383 A | 5/1987 | Sogawa et al. | |
| 4,739,759 A | 4/1988 | Rexroth et al. | |
| 4,832,024 A | 5/1989 | Boussignac et al. | |
| 4,880,719 A | 11/1989 | Murofushi et al. | |
| 4,961,435 A | 10/1990 | Kitagawa et al. | |

(Continued)

FOREIGN PATENT DOCUMENTS

| DE | 2407559 | | 2/1974 |
|---|---|---|---|
| EP | 0171967 | A | 2/1986 |

(Continued)

OTHER PUBLICATIONS

Cosman ER. Cosman BJ: "Methods of Making Nervous System Lesions", in William RH, Rengachary SS (eds): Neurosurgery. New York: McGraw-Hill, vol. 111, pp. 2490-2498, 1984.

(Continued)

*Primary Examiner* — Michael Peffley
*Assistant Examiner* — Samantha Good (57) ABSTRACT

An electrosurgical system and method for performing an electrosurgical procedure are disclosed. The electrosurgical system includes a high frequency generator to supply energy, the generator including one or more electrical connections. The system also includes one or more instruments configured to be inserted into tissue of the patient's body having a hardened tissue volume. The instruments are configured to penetrate the hardened tissue volume to create at one or more orifices defined therein. The instruments are also configured to selectively encapsulate one or more active electrodes that are coupled to the electrical connections. Each of the electrodes has an elongated shaft terminating in an exposed, conductive tip. The electrodes are configured to be inserted into the tissue of the patient's body and into the hardened tissue volume through the orifices to subsequently apply energy from the high frequency generator to the exposed, conductive tip to induce a coherent heating effect in the hardened tissue volume from power deposition therein, thereby producing a heat ablation volume in the hardened tissue volume.

17 Claims, 4 Drawing Sheets

(56) References Cited

U.S. PATENT DOCUMENTS

| | | | |
|---|---|---|---|
| 4,966,597 A | 10/1990 | Cosman | |
| 4,993,430 A | 2/1991 | Shimoyama et al. | |
| 5,011,483 A * | 4/1991 | Sleister | 606/37 |
| 5,029,588 A | 7/1991 | Yock et al. | |
| 5,103,804 A | 4/1992 | Abele et al. | |
| 5,225,741 A | 7/1993 | Auld et al. | |
| 5,230,623 A | 7/1993 | Guthrie et al. | |
| 5,267,994 A | 12/1993 | Gentelia et al. | |
| 5,281,213 A | 1/1994 | Milder et al. | |
| 5,323,778 A | 6/1994 | Kandarpa et al. | |
| 5,330,518 A | 7/1994 | Neilson et al. | |
| 5,334,193 A | 8/1994 | Nardella | |
| 5,342,357 A | 8/1994 | Nardella | |
| 5,348,554 A | 9/1994 | Imran et al. | |
| 5,370,675 A | 12/1994 | Edwards et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A | 4/1995 | Abele et al. | |
| 5,409,000 A | 4/1995 | Imran | |
| 5,409,006 A | 4/1995 | Buchholtz et al. | |
| 5,433,739 A | 7/1995 | Sluijter et al. | |
| 5,458,597 A | 10/1995 | Edwards et al. | |
| 5,462,521 A | 10/1995 | Brucker et al. | |
| 5,472,441 A | 12/1995 | Edwards et al. | |
| 5,490,850 A | 2/1996 | Ellman et al. | |
| 5,500,012 A | 3/1996 | Brucker et al. | |
| 5,520,684 A | 5/1996 | Imran | |
| 5,536,267 A | 7/1996 | Edwards et al. | |
| 5,571,147 A | 11/1996 | Sluijter et al. | |
| 5,588,432 A | 12/1996 | Crowley | |
| 5,599,345 A | 2/1997 | Edwards et al. | |
| 5,647,871 A | 7/1997 | Levine et al. | |
| 5,662,111 A | 9/1997 | Cosman | |
| 5,688,267 A | 11/1997 | Panescu et al. | |
| 5,735,847 A | 4/1998 | Gough et al. | |
| 5,775,338 A | 7/1998 | Hastings | |
| 5,792,146 A | 8/1998 | Cosman | |
| 5,848,967 A | 12/1998 | Cosman | |
| 5,849,011 A | 12/1998 | Jones et al. | |
| 5,868,740 A | 2/1999 | LeVeen et al. | |
| 5,921,982 A | 7/1999 | Lesh et al. | |
| 5,951,546 A | 9/1999 | Lorentzen | |
| 6,001,093 A | 12/1999 | Swanson et al. | |
| 6,006,126 A | 12/1999 | Cosman | |
| 6,053,912 A | 4/2000 | Panescu et al. | |
| 6,059,780 A | 5/2000 | Gough et al. | |
| 6,061,551 A | 5/2000 | Sorrells et al. | |
| 6,074,389 A | 6/2000 | Levine et al. | |
| 6,080,149 A | 6/2000 | Huang et al. | |
| 6,106,524 A | 8/2000 | Eggers et al. | |
| 6,146,380 A | 11/2000 | Racz et al. | |
| 6,162,216 A | 12/2000 | Guziak et al. | |
| 6,203,541 B1 | 3/2001 | Keppel | |
| 6,241,725 B1 | 6/2001 | Cosman | |
| 6,287,305 B1 | 9/2001 | Heim et al. | |
| 6,306,132 B1 | 10/2001 | Moorman et al. | |
| 6,337,998 B1 | 1/2002 | Behl et al. | |
| 6,478,793 B1 | 11/2002 | Cosman et al. | |
| 6,500,172 B1 | 12/2002 | Panescu et al. | |
| 6,506,189 B1 | 1/2003 | Rittman, III et al. | |
| 6,530,922 B2 | 3/2003 | Cosman et al. | |
| 6,575,969 B1 | 6/2003 | Rittman, III et al. | |
| 6,605,085 B1 | 8/2003 | Edwards | |
| 6,852,110 B2 * | 2/2005 | Roy et al. | 606/41 |
| 2001/0034518 A1 | 10/2001 | Edwards et al. | |
| 2002/0111615 A1 | 8/2002 | Cosman et al. | |
| 2002/0120261 A1 | 8/2002 | Morris et al. | |
| 2002/0156472 A1 | 10/2002 | Lee et al. | |
| 2003/0195517 A1 * | 10/2003 | Michelson | 606/79 |
| 2004/0002745 A1 | 1/2004 | Fleming et al. | |
| 2004/0039429 A1 | 2/2004 | Daniel et al. | |
| 2004/0059328 A1 * | 3/2004 | Daniel et al. | 606/41 |
| 2004/0181216 A1 | 9/2004 | Kelly et al. | |
| 2004/0254573 A1 | 12/2004 | Dycus | |
| 2005/0107784 A1 | 5/2005 | Moses | |
| 2005/0107785 A1 | 5/2005 | Dycus | |
| 2005/0119655 A1 | 6/2005 | Moses | |
| 2005/0154387 A1 | 7/2005 | Moses | |
| 2005/0155743 A1 | 7/2005 | Getz, Jr. et al. | |
| 2005/0192564 A1 | 9/2005 | Cosman et al. | |
| 2006/0041257 A1 | 2/2006 | Sartor et al. | |
| 2006/0079885 A1 | 4/2006 | Rick et al. | |
| 2006/0079886 A1 | 4/2006 | Orszulak | |
| 2006/0079887 A1 | 4/2006 | Buysse | |

FOREIGN PATENT DOCUMENTS

| | | |
|---|---|---|
| EP | 0246350 | 11/1987 |
| EP | 0310431 | 4/1989 |
| EP | 0608609 | 8/1994 |
| EP | 1465037 A | 10/2004 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 99/01074 | 1/1999 |
| WO | WO 99/04710 | 2/1999 |
| WO | WO 01/00114 A1 | 1/2001 |
| WO | WO 2005/009528 | 2/2005 |

OTHER PUBLICATIONS

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedance", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with SpeCial Applicators for High-Frequency Interstitial Thermotherapy". Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et al., "Image-guided Radiofrequency Tumor Ablation: Challenges and Opportunities—Part I", (200I) *J Vasc. Interv. Radiol*, vol. 12, pp. 1021-1032.

McGahan et al. (1995) "Percutaneous Ultrasound-guided Radiofrequency Electrocautery Ablation of Prostate Tissue in Dogs", Acad Radiol, vol. 2, No. 1:pp. 61-65.

(56) References Cited

OTHER PUBLICATIONS

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

\* cited by examiner

SYSTEM AND METHOD FOR ABLATING TISSUE

BACKGROUND

1. Field

The present disclosure relates generally to an electrosurgical system and method and, more specifically, to a system and method for ablating impenetrable abnormal tissue.

2. Description of the Related Art

The use of radiofrequency electrodes for ablation of tissue in a patient's body is known. In a typical situation, a radiofrequency electrode having an elongated, cylindrical shaft with a portion of its external surface insulated is inserted into the patient's body. The electrode typically has an exposed conductive tip, which is used to contact body tissue in the region where the heat lesion or ablation is desired. The electrode is connected to a radiofrequency power source that provides radiofrequency voltage to the electrode, which, in turn, transmits the radiofrequency current into the tissue near its exposed conductive tip. This current usually returns to the power source through a return electrode, which may comprise a large area conductive contact connected to an external portion of the patient's body. This configuration has been described in various scientific articles, such as, for example, a research paper by Cosman, et al., entitled "Theoretical Aspects of Radiofrequency Lesions in the Dorsal Root Entry Zone," Neurosurgery, December 1984, Vol. 15, No. 6, pp 945-950, and a research paper by Goldberg, et al. entitled "Tissue Ablation with Radiofrequency: Effective Probe Size, Gauge, Duration, and Temperature and Lesion Volume" Acad Radio., 1995, Vol. 2, No. 5, pp 399-404. Radiofrequency lesion generators and electrode systems such as those described above are commercially available from Radionics, Inc., located in Burlington, Mass.

It is also known to use radiofrequency electrodes to ablate tumors. However, certain types of tumors, such as some solid tissue tumors typically cannot be easily penetrated with medical instruments (e.g., biopsy needles, electrodes, etc.) and therefore cannot be directly ablated. Conventional practices to solve this issue involve ablating healthy tissue surrounding the tumors, which tend to ablate the impenetrable tumors in the process. Such procedures have undesirable consequences, such as delocalized damage to surrounding healthy tissue.

SUMMARY

The present disclosure provides for a system and method for ablating tissue. In particular, the disclosure is directed to ablation of tumors that cannot be penetrated by ablation electrodes. Initially, an orifice is created within the tumor to accommodate an ablation electrode. The ablation electrodes are then inserted into the tumor through the corresponding orifice and the tumor is ablated.

An electrosurgical system and method for performing an electrosurgical procedure are disclosed. The electrosurgical system includes a high frequency generator to supply energy, the generator including one or more electrical connections. The system also includes one or more instruments configured to be inserted into tissue of the patient's body having a hardened tissue volume. The instruments are configured to penetrate the hardened tissue volume to create at one or more orifices defined therein. The instruments are also configured to selectively encapsulate one or more active electrodes that are coupled to the electrical connections. Each of the electrodes has an elongated shaft terminating in an exposed, conductive tip. The electrodes are configured to be inserted into the tissue of the patient's body and into the hardened tissue volume through the orifices to subsequently apply energy from the high frequency generator to the exposed, conductive tip to induce a coherent heating effect in the hardened tissue volume from power deposition therein, thereby producing a heat ablation volume in the hardened tissue volume.

According to another aspect of the present disclosure, a method for performing an electrosurgical procedure is disclosed. The method includes the steps of providing an instrument configured to removably encapsulate an active electrode disposed on an elongated shaft. The active electrode is adapted to couple to an electrical energy source and includes an exposed, conductive tip. The instrument is configured to penetrate a hardened tissue volume to create at an orifice defined therein. The method also includes the steps of inserting the instrument into a hardened tissue volume to create the orifice defined therein and removing the instrument from the active electrode. The method further includes the steps of inserting the active electrode into the orifice defined in the hardened tissue volume and activating the active electrode to apply energy from the electrical energy source to induce a coherent heating effect in the hardened tissue volume from power deposition therein thereby producing a heat ablation volume in the hardened tissue volume.

According to a further aspect of the present disclosure, an ablation probe is disclosed. The ablation probe includes an active electrode having an elongated shaft and being adapted to connect to an electrical energy source. The probe also includes a boring device configured to removably encapsulate said at least one active electrode. The boring device is configured to penetrate a hardened tissue volume to create an orifice defined therein such that, after removal of the boring device, the active electrode can be subsequently inserted into said orifice and activated to induce a coherent heating effect in the hardened tissue volume from power deposition therein thereby producing a heat ablation volume in the hardened tissue volume.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Embodiments of the present disclosure are described herein below with reference to the accompanying drawings. In the following description, well-known functions or constructions are not described in detail to avoid obscuring the present disclosure in unnecessary detail.

Figure 1:
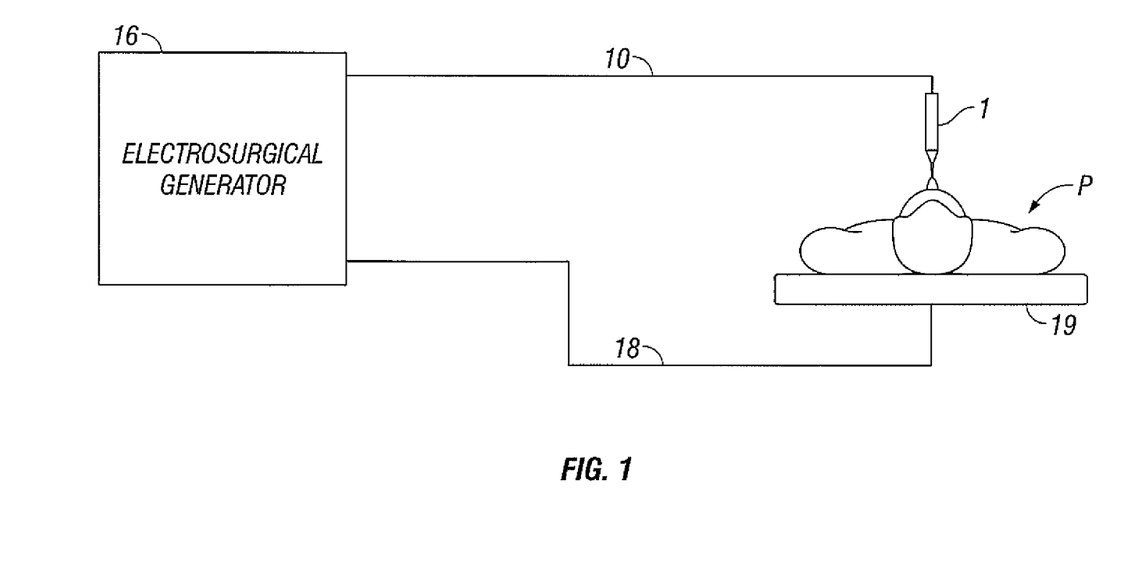
FIG. 1 is a schematic block diagram of a monopolar electrosurgical system.

FIG. 1 is a schematic illustration of an electrosurgical system configured for a monopolar procedure, such as ablation of tumors. The system includes an active electrode 1 and a return electrode 19 for treating tissue of a patient P. Electrosurgical RF energy is supplied to the active electrode 1 by a generator 16 via a cable 10 allowing the active electrode 1 to ablate, cut or coagulate the tissue. The active electrode 1 is typically part of the surgical instrument held by the surgeon and applied to the tissue to be treated.

In monopolar electrosurgery, the active electrode 1 delivers radio frequency energy from the electrosurgical generator 16 to the tissue and a return electrode carries the current back to the generator. The return electrode 19 is typically remotely placed relative to the active electrode 1 under the patient P to return the energy from the patient P to the generator 16 via a cable 20.

The generator 16 includes input controls (e.g., buttons, activators, switches, etc.) for controlling the generator 16. The controls allow the surgeon to adjust power of the RF energy, waveform, and other parameters to achieve the desired waveform suitable for a particular task (e.g., cutting, coagulating, etc.). The active electrode 1 may be incorporated into a hand piece that includes controls for adjusting output of the generator 16.

The hand piece may be disposed between the generator 16 and the active electrode 1 on the cable 20 and may include a plurality of input controls that may be redundant with certain input controls of the generator 16. Placing the input controls at the hand piece allows for easier and faster modification of RF energy parameters during the surgical procedure without returning to the generator 16. The hand piece and the electrode 1 may also be incorporated into a single instrument, e.g. a surgical pencil, with the electrode 1 being disposed at a distal end of the hand piece. An exemplary embodiment of an electrosurgical instrument having a hand piece and an active electrode is disclosed in a commonly owned U.S. patent application Ser. No. 11/198,473 entitled "Electrosurgical Pencil With Improved Controls" which is hereby incorporated by reference herein. A footswitch may also be connected to the generator to control energy delivery during monopolar procedures.

Figure 2:
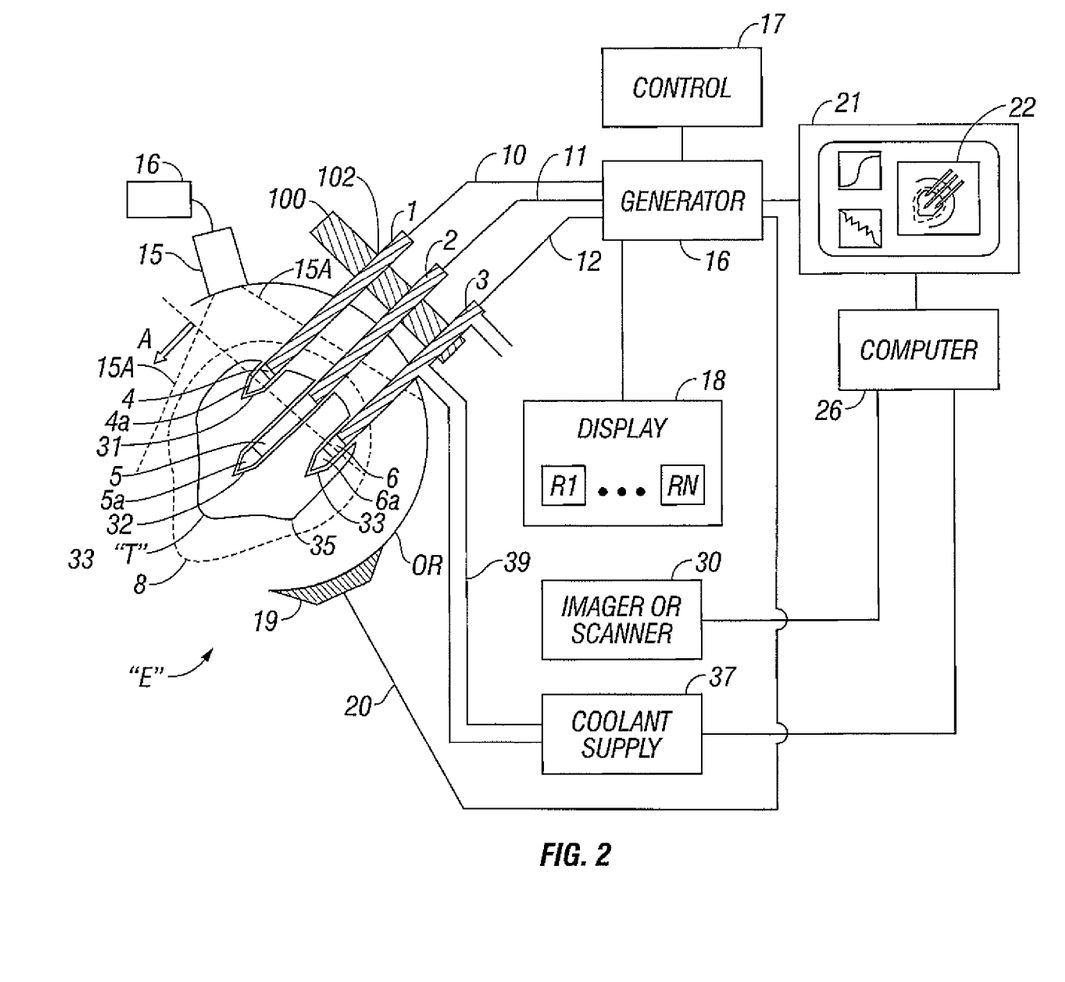
FIG. 2 is a schematic block diagram of an embodiment of an electrosurgical system according to the present disclosure.

FIG. 2 shows an embodiment of the electrosurgical system in accordance with the present disclosure, wherein the system comprises one or more active electrodes arranged in a coherent cluster electrode system E. The cluster electrode system E comprises a plurality of electrodes 1, 2 and 3, that are inserted into an organ OR, which may represent any organ in a human body. The distal ends 4, 5 and 6 of the electrodes 1, 2 and 3, respectively, are uninsulated and conductively exposed so that electrical currents induce heating within the tissue or organ OR. A targeted volume of tissue T is shown in sectional view, which may represent, for example, a tumor or other abnormality in a human body.

The electrodes 1, 2 and 3, are coupled by wires or cables 10, 11 and 12, as shown, to a generator 16. The generator 16 may be any suitable radiofrequency or high frequency type of generator. The generator 16 has control elements, illustrated generally by block 17, which may, for example, increase the radiofrequency power output to the electrodes, control temperature when the cluster electrode system E or satellite sensors comprise temperature sensors, monitor or control impedance, power, current, voltage, or other output parameters. The generator 16 may include a display provision, illustrated by block 18, within the generator 16 or as a separate system for providing a display of heating parameters such as temperature for one or more of the electrodes, impedance, power, current, or voltage of the radiofrequency output. Such individual display readings are illustrated by the reference letters R1, . . . to RN.

The return electrode 19 is also shown and may be placed in contact with the skin of a patient or the external surface of the organ OR with a connection 20 to the generator 16. More than one return electrode 19 may be used to maximize contact with the patient and thereby minimize the chance of onsite tissue damage.

The electrodes 1, 2 and 3, in accordance with one exemplary embodiment, include rigid shafts having distal ends 4, 5 and 6 that may be easily inserted into the body tissue. Each electrode 1, 2 and 3 terminates in a removably engageable tissue-penetrating pointed tip, respectively, 4a, 5a and 6a on the distal ends 4, 5, and 6 thereof. The distal ends 4, 5 and 6 for each electrode 1, 2 and 3 comprise conductive metal and are connected to connection cables 10, 11 and 12, respectively, which ultimately connect to the generator 16.

By way of one specific example, the generator 16 may be a radiofrequency generator having a frequency range between about 100 kHz to several hundred mHz. An example of such a generator is the lesion generator available from Radionics, Inc., of Burlington, Mass., which has a power output ranging from several watts to several hundred watts, depending on the clinical application.

According to the present disclosure and illustrated in FIG. 2, the distal ends 4, 5 and 6 may be energized to the same radiofrequency voltage potential from generator 16. The cluster of electrodes in essence becomes, in effect, a larger, coherent electrode comprising the individual distal ends 4, 5, and 6. Thus, the overall heating effect is similar to that accomplished by one large, single electrode. With the cluster electrode system of the present disclosure, the individual distal ends 4, 5 and 6 tend to cause less trauma to tissue, thus limiting hemorrhaging when the distal ends 4, 5 and 6 of the electrodes 1, 2 and 3 penetrate the organ OR because of their smaller size. Yet when they are connected to a coherent, parallel voltage level, they represent an effectively much larger electrode. In this way, larger heat volumes, and therefore ablation sizes, may be achieved.

As an illustration, a targeted volume (e.g., tumor T) is shown in FIG. 2. It may be desired to ablate the tumor T by fully engulfing the tumor in a volume of lethal heat elevation. The tumor T may be, for example, a tumor that has been detected by image scanner 30. CT, MRI, or ultrasonic image scanners may be used, and the image data is transferred to computer 26. As an alternate example, an ultrasonic scanner head 15 may be disposed in contact with OR to provide an image illustrated by lines 15A. A data processor 16 may be connected to display devices to visualize the tumor T and/or ablation zone 8 in real-time during the ablation procedure. The image representation of the scan may be displayed on display unit 21, which may, for example, be a CRT screen. Slice renderings through the organ OR may be displayed in window 22 to represent the size and position of the tumor T. Placement of the electrode distal ends 4, 5 and 6 may be predetermined based on such image data as interactively determined by real-time scanning of organ OR. The electrodes 1, 2 and 3 are typically inserted into the tissue by a freehand technique using a guide block with multiple template hole, or by a stereotactic frame or by frameless guidance, e.g., by stereotactic instruments made by Radionics, Inc., of Burlington, Mass. A stereotactic guide is shown schematically by element 100. Guide holes such as 102 for electrodes 1, 2 and 3 aim the electrode(s) 1, 2 and 3 to a desired targeted position based on image data.

As shown in FIG. 2, a cluster of electrodes 1, 2 and 3 is connected to the same radiofrequency voltage from generator 16. As mentioned above, the electrodes 1, 2 and 3 act as an effectively larger electrode and the relative positions and orientations of the electrodes 1, 2 and 3 enable the surgeon to ablate varying volumes of tissue. For example, the dashed line represents the ablation isotherm in a sectional view through organ OR. Such an ablation isotherm may be the surface achieving temperatures of approximately 50 degrees or greater. At that temperature range, sustained for about 30 seconds to several minutes, tissue cells are typically ablated. The shape and size of the ablation volume illustrated by dashed line 8 may accordingly be controlled by the configuration of the electrode cluster, the geometry of the exposed distal ends 4, 5 and 6, the amount of RF power applied, the duration that the power is applied, the cooling of the electrodes, etc.

The system E also includes a coolant supply 37 that provides cooling fluid (e.g., saline solution at or below room temperature) to the electrodes 1, 2 and 3 to remove heat generated therein. Coolant supply 37 is controlled by a computer 26 based on a plurality of feedback signals (e.g., measured tissue impedance and/or temperature). The coolant fluid flows through an internal cavity defined in electrodes 1, 2 and 3 thereby withdrawing heat from the electrodes 1, 2 and 3 as well as the surrounding tissue during activation. The coolant fluid flows to the electrodes 1, 2 and 3 through a coolant supply line 39.

Figure 4:
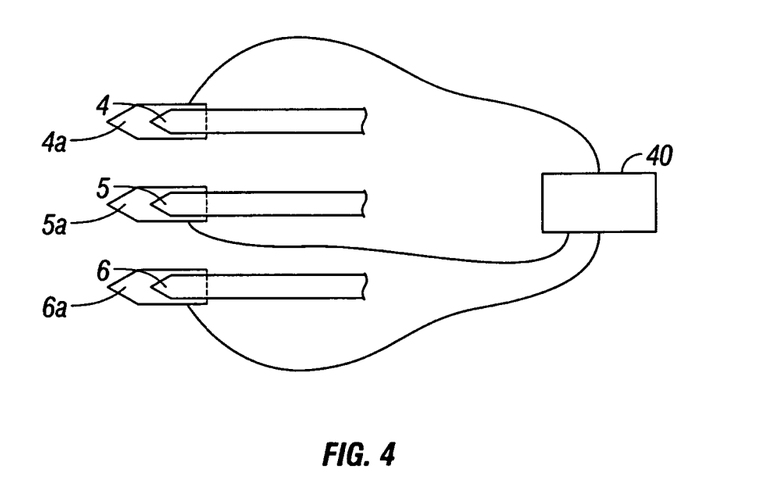
FIG. 4 is a schematic block diagram of instruments for penetrating tissue according to the present disclosure.

With continued reference to FIG. 2, tumor T may in certain instances be difficult to penetrate by simply pushing the electrodes 1, 2 and 3 into the tumor. As mentioned above, the distal ends 4, 5 and 6 of electrodes 1, 2 and 3 include removably engageable tissue penetrating tips 4a, 5a and 6a disposed thereon. These boring devices or tips 4a, 5a and 6a are made of hard, substantially rigid material and are configured to encapsulate each distal ends 4, 5 and 6. The tips 4a, 5a and 6a allow the surgeon to force the instrument into the tumor T to create orifices in the tumor T for subsequent ablation. The tips 4a, 5a and 6a may be electrically conductive, ultrasonic or the like to facilitate penetration of the tumor T. The tips 4a, 5a and 6a may also be operatively coupled to a laser or ultrasonic element to facilitate penetration of the tumor T as shown in FIG. 4. In particular, a laser drill may be used to create precise incisions for the orifices 31, 32 and 33. The tips 4a, 5a and 6a may also be chemically enhanced to facilitate insertion of the tips 4a, 5a and 6a through the hardened tissue volume.

FIG. 4 shows selectively engageable tips 4a, 5a and 6a with distal ends 4, 5 and 6 of the electrodes 1, 2 and 3, respectively. The tips 4a, 5a and 6a may engage the distal ends 4, 5 and 6, respectively using any suitable mechanical means (e.g., threads, interlocking mechanisms, etc.). The tips 4a, 5a and 6a may also be operably connected to a power source 40 configured for supplying energy to the tips 4a, 5a and 6a, which is then converted to corresponding energy (e.g., laser or ultrasonic) by the tips 4a, 5a and 6a. The tips 4a, 5a and 6a may be connected to the same energy source as the active electrodes 1, 2 and 3, i.e., generator 16, may be computer controlled and/or may be separately connected to an alternative energy source depending upon a particular purpose. The tips 4a, 5a and 6a may also be separately activatable relative to the active electrodes or may be activated through activation of the active electrodes, e.g., the RF energy may be converted to an alternate energy source to penetrate the hardened tissue volume. Those skilled in the art will appreciate that to apply laser energy the tips 4a, 5a and 6a may include additional components for focusing the beam (e.g., lenses). In order to convert ultrasonic energy at the tips 4a, 5a and 6a, it may be necessary to employ additional components, e.g., transducers, ultrasonic probes, etc., which are within the purview of those skilled in the art.

A computer and/or visual display may be used to regulate the depth of the orifice while penetrating the tumor T. The same or different components may be used to regulate the ablation volume as well. The depth and ablation volume may be regulated automatically by the computer based on a variety of suitable feedback measurements.

The tips 4a, 5a or 6a may also include a chemical coating or be configured to allow the infusion of a chemical substance to facilitate penetration of the tumor T. Orifices in the tumor T may be created by ablating portions of the surface of the tumor T using specially configured tips 4a, 5a and 6a that contact the shell 35 and create arcing between each tips 4a, 5a and 6a and the surface of the tumor T. In other words, the tips 4a, 5a and 6a are configured to concentrate energy at the points to bore orifices 31, 32 and 33 in the tumor T, which are subsequently advanced into the tumor T to a desired orifice depth.

Other energy delivery devices may be used to create the orifices 31, 32, 33. These devices may be distinct and separate from the electrodes 1, 2, 3 and may be introduced into the organ OR prior to ablation to create the orifices 31, 32, 33. Envisioned energy delivery devices may include laser drills and ultrasonic probes. Other mechanical and/or chemical devices that are attachable to the active electrodes may be used to create the orifices 31, 32, 33, such as, for example, a drilling device or a syringe depositing a chemical substance suitable for destroying tissue of the tumor T. Still other separate drilling or boring devices are also envisioned that will create orifices in the hardened tissue volume, which do not necessarily attach to the active electrodes 1, 2 and 3.

Once the tumor T has been successfully penetrated by the tips 4a, 5a and 6a, the surgeon removes the instruments from the tumor and removes the tips 4a, 5a, and 6a and reinserts the electrodes 1, 2 and 3 into the tumor to ablate the tumor T as mentioned above.

Figure 3:
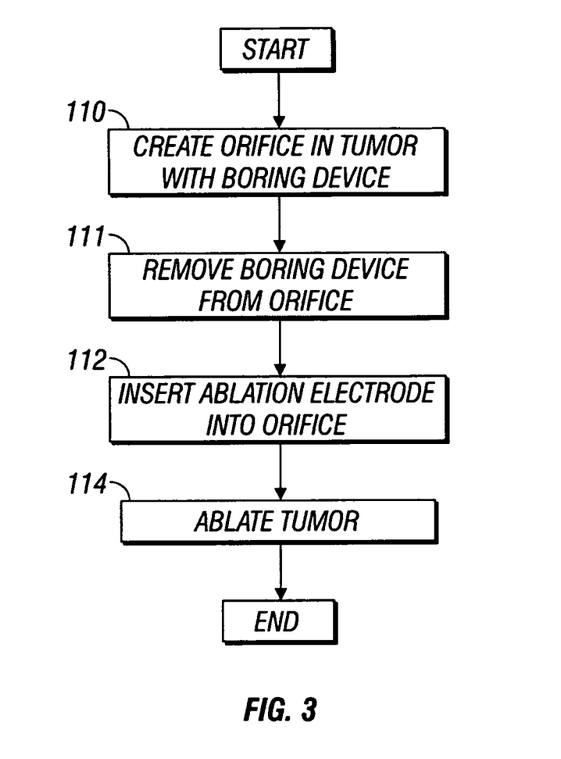
FIG. 3 is a flow diagram illustrating a method according to the present disclosure.

FIG. 3 shows a method according to the present disclosure to ablate such tumors T. In step 110 orifices 31, 32 and 33 are created within the tumor T. As mentioned above, the orifices 31, 32 and 33 may be created in a variety of ways. The depth of the orifice may also be computer controlled and regulated.

In step 111, the orifice boring device(s) are removed from the orifice and/or from the active electrode(s). In step 112, the electrodes 1, 2, 3 are inserted into the orifices 31, 32, 33, respectively. The depth of insertion of the electrodes 1, 2, 3 into the tumor T may be monitored via the window 22 showing the slice view of the organ OR. Optimum positioning of the electrodes 1, 2 and 3 within the tumor T and in particular the electrode tips 4, 5 and 6 allows for efficient ablation of the tumor T without destroying surrounding healthy tissue of the organ OR.

In step 114, the tumor T is ablated by supplying electrosurgical RF energy from the generator 16 to the electrode tips 4, 5 and 6. Parameters of the electrosurgical RF energy may be adjusted manually and/or automatically via the help of the computer 26. For instance, tissue parameters may be input into the computer 26, which then calculates optimum energy application parameters (e.g., power, duration application, etc.). Energy application parameters may be loaded automatically based upon measured tissue properties (e.g., initial measured tissue impedance).

The ablation step 114 may include one or more stages wherein energy is applied to the tumor T in sequences. After an initial sequence, the electrode tips 4, 5, 6 are rearranged (e.g., adjusting depth, creating new orifices in the tumor T and inserting the electrodes 1, 2, 3) to modify the ablation volume. This may be repeated until a desired ablation volume is achieved.

Figure 5:
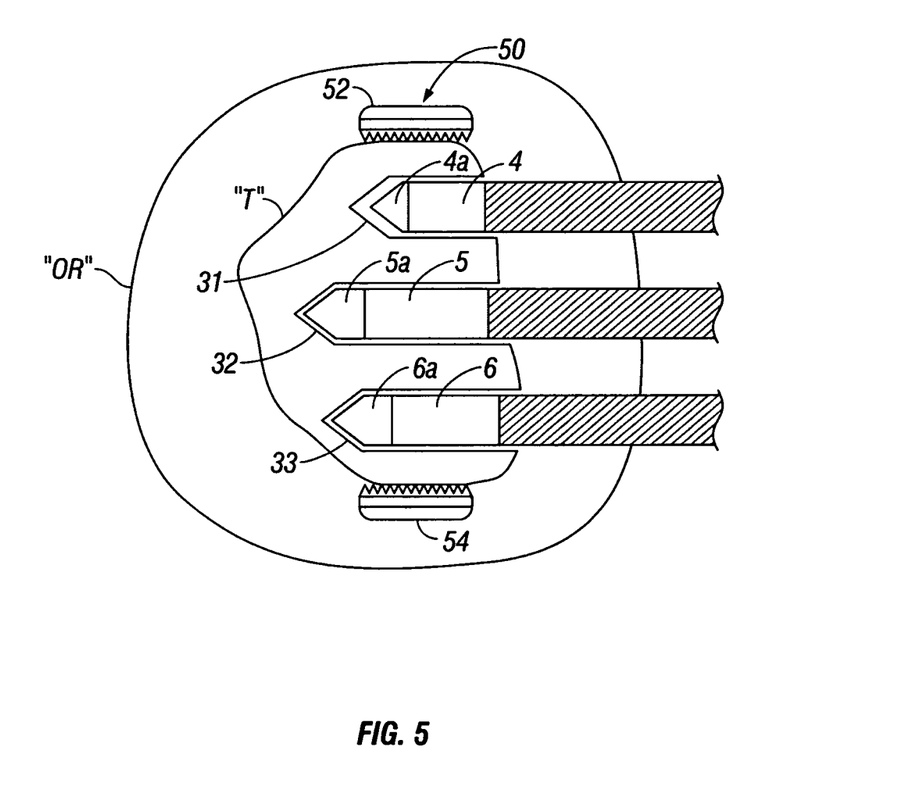
FIG. 5 is a schematic block diagram of another embodiment of an electrosurgical system according to the present disclosure.

Another embodiment of the present disclosure is further illustrated in FIG. 5 wherein a grasping instrument 50 is used to stabilize the tumor T within the organ OR. The grasping instrument 50 includes two or more jaw members 52, 54, which are used to grasp the tumor T and hold the tumor T in place. This stabilizes the tumor T and prevents the tumor T sliding out of place as orifices 31, 32 and 33 are created or as the electrodes 4, 5 and 6 are inserted therein. The grasping instrument 50 may be an endoscopic deployable instrument or an open instrument. The step of grasping the tumor T may be performed prior to or concurrently with drilling of the orifices 31, 32 and 33.

The present disclosure may be adapted for use with a bipolar electrosurgical arrangement wherein active and return electrodes are disposed in relative proximity to each other. One or more of the electrodes 4, 5 and 6 is configured as an active electrode and one or more of the remaining electrodes 4, 5 and 6 is configured as a return electrode. The electrodes 4, 5 and 6 are inserted into the tumor T in the manner discussed above; however, energy is provided to some of the electrodes while allowing other electrodes to act as return electrodes. Utilizing the electrodes 4, 5 and 6 in a bipolar fashion allows for the formation of non-circular shaped lesions. This is particularly useful in ablating abnormally shaped relatively impenetrable tumors.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. An electrosurgical system, comprising:
   a high frequency generator including at least one electrical connection;
   at least one instrument including;
      a plurality of electrodes, each of the plurality of electrodes including an elongated shaft having an exposed, conductive distal end coupled to the at least one electrical connection such that each electrode of the plurality of electrodes is energized at a same radiofrequency voltage potential from the high frequency generator; and
      a plurality of removably engageable, tissue-penetrating tips each having a closed distal end configured to be inserted into tissue of a patient's body having a hardened tissue volume and configured to penetrate the hardened tissue volume to create a plurality of orifices defined therein, wherein each of the tips are removably engageable with the at least one instrument using at least one of a threadable or interlocking connection and each of the tips selectively encapsulates the conductive distal end of each of the plurality of electrodes;
      wherein the plurality of electrodes are configured to be inserted into the tissue of the patient's body and into the hardened tissue volume through the plurality of orifices to subsequently apply energy from the high frequency generator to the conductive distal ends to induce a coherent heating effect in the hardened tissue volume from power deposition therein thereby producing a heat ablation volume in the hardened tissue volume; and
   a computer configured to selectively regulate an insertion depth of the at least one instrument to selectively adjust a depth of the plurality of orifices.

2. An electrosurgical system according to claim 1, wherein each of the tips are is selected from the group consisting of a laser, an ultrasonic tissue penetrating element and a chemically-enhanced tip.

3. An electrosurgical system according to claim 1, wherein each electrode of the plurality of electrodes includes an internal cavity configured for circulation of a coolant fluid supplied by a coolant supply.

4. An electrosurgical system according to claim 1, wherein the computer configured to regulate the energy from the high frequency generator to adjust the heat ablation volume.

5. An electrosurgical system according to claim 1, further comprising a grasping instrument that stabilizes the hardened tissue volume within the patient's body.

6. An electrosurgical system according to claim 1, wherein the distal ends of the plurality of electrodes are coupled to a generator configured to supply a parallel voltage level.

7. A method for performing an electrosurgical procedure comprising the steps of:
   encapsulating exposed, conductive distal ends of a plurality of electrodes with removably engageable, tissue-penetrating tips each having a closed distal end, wherein each electrode of the plurality of electrodes is disposed on an elongated shaft of at least one instrument configured to penetrate a hardened tissue volume and each of the tips are removably engageable with the distal ends of the plurality of electrodes using at least one of a threadable or interlocking connection;
   coupling the plurality of electrodes to an electrical energy source such that each electrode of the plurality of electrodes is energized at a same radiofrequency voltage potential from the electrical energy source;
   inserting the tips into the hardened tissue volume to create a plurality of orifices defined therein;
   removing the tips from the distal ends of the plurality of electrodes;
   inserting the distal ends of the plurality of electrodes into the plurality of orifices defined in the hardened tissue volume;
   activating the plurality of electrodes to apply energy from the electrical energy source to induce a coherent heating effect in the hardened tissue volume from power deposition therein thereby producing a heat ablation volume in the hardened tissue volume; and
   selectively regulating a depth of insertion of the at least one instrument into the hardened tissue volume via a computer.

8. A method according to claim 7, wherein each of the tips is selected from the group consisting of a laser, an ultrasonic tissue penetrating element and a chemically-enhanced tip.

9. A method according to claim 7, wherein each of the tips is selected from the group consisting of a laser and an ultrasonic tissue penetrating element that is connected to the electrical energy source.

10. A method according to claim 7, wherein each of the tips is selected from the group consisting of a laser and an ultrasonic tissue penetrating element that is connected to a separate electrical energy source.

11. A method according to claim 7, wherein each of the tips is selected from the group consisting of a laser and an ultrasonic tissue penetrating element that is connected and independently activatable from the at least one active electrode.

12. A method according to claim 7, further comprising circulating a coolant fluid through an internal cavity of each electrode of the plurality of electrodes.

13. A method according to claim 7, further comprising automatically regulating the energy from the electrical energy source to adjust the ablation volume via a computer.

14. A method according to claim 7, further comprising stabilizing the hardened tissue volume within the patient's body.

15. A method according to claim 7, wherein the distal ends of the plurality of electrodes are coupled to a generator configured to supply a parallel voltage level.

16. An ablation probe, comprising:
a plurality of electrodes, each electrode of the plurality of electrodes having an elongated shaft, the plurality of electrodes being adapted to connect to an electrical energy source such that each electrode of the plurality of electrodes is energized at a same radiofrequency voltage potential from the electrical energy source;
a plurality of removably engageable, tissue-penetrating boring devices each having a closed distal end and each being configured to selectively encapsulate a distal end of one electrode of the plurality of electrodes, wherein each of the boring devices includes at least one of a threadable or interlocking connection for removably engaging with each of the distal ends of the electrodes, the boring devices are configured to penetrate a hardened tissue volume to create a plurality of orifices defined therein such that, after removal of the boring devices, the plurality of electrodes can be subsequently inserted into the plurality of orifices and activated to induce a coherent heating effect in the hardened tissue volume from power deposition therein thereby producing a heat ablation volume in the hardened tissue volume, wherein each of the removably engageable boring devices includes a laser.

17. The ablation probe according to claim 16, wherein the distal ends of the plurality of electrodes are coupled to a generator configured to supply a parallel voltage level.

* * * * *